(12) United States Patent
Knutsson

(10) Patent No.: US 11,202,887 B2
(45) Date of Patent: Dec. 21, 2021

(54) NEEDLE TIP SHIELDING DEVICE AND CATHETER HUB THEREFORE

(71) Applicant: Vigmed AB, Helsingborg (SE)

(72) Inventor: Per Knutsson, Helsingborg (SE)

(73) Assignee: VIGMED AB, Helsingborg (SE)

( * ) Notice: Subject to any disclaimer, the term of this patent is extended or adjusted under 35 U.S.C. 154(b) by 6 days.

(21) Appl. No.: 15/565,343

(22) PCT Filed: Apr. 7, 2016

(86) PCT No.: PCT/SE2016/050295
§ 371 (c)(1),
(2) Date: Oct. 9, 2017

(87) PCT Pub. No.: WO2016/163939
PCT Pub. Date: Oct. 13, 2016

(65) Prior Publication Data
US 2018/0304048 A1    Oct. 25, 2018

(30) Foreign Application Priority Data

Apr. 9, 2015    (SE) .................................... 1550419-4

(51) Int. Cl.
*A61M 25/06*    (2006.01)
*A61M 5/32*    (2006.01)
(Continued)

(52) U.S. Cl.
CPC ...... *A61M 25/0618* (2013.01); *A61M 5/3221* (2013.01); *A61M 25/0097* (2013.01);
(Continued)

(58) Field of Classification Search
CPC .......... A61M 25/0606; A61M 25/0618; A61M 5/3221; A61M 5/1626; A61M 2005/3226;
(Continued)

(56) References Cited

U.S. PATENT DOCUMENTS 4,929,241 A * 5/1990 Kulli ................... A61M 5/3243
604/110
5,135,504 A * 8/1992 McLees .............. A61M 5/3273
604/164.08
(Continued)

FOREIGN PATENT DOCUMENTS

AU    2013278960 A1    1/2015
CN    102958553 A    3/2013
(Continued)

OTHER PUBLICATIONS

Supplementary European Search Report; Application No. EP16776993 dated Jan. 25, 2019.
(Continued)

*Primary Examiner* — Theodore J Stigell
(74) *Attorney, Agent, or Firm* — Fishman Stewart PLLC

(57) ABSTRACT

A needle tip shielding device, comprising a base plate with a hole extending there through from the proximal side of the base plate to the distal side of the base plate, and at least one resilient arm extending at an attachment point at said base plate (101) is provided. The resilient arm has a resting state wherein a distal hook of the resilient arm will coincide with a straight imaginary line extending longitudinally through said hole in the axial direction of said base plate. The resilient arm comprises a knob at its distal end, said knob extending laterally from the resilient arm. The knob is shaped with an outer curvature in the transversal plane around an axis parallel to the central axis of the needle tip shielding device and said knob is shaped with an outer curvature in the midsaggital plane around an axis perpendicular to the central axis of the needle tip shielding device.

19 Claims, 6 Drawing Sheets

(51) Int. Cl.
 *A61M 25/00* (2006.01)
 *A61M 5/162* (2006.01)
(52) U.S. Cl.
 CPC ....... *A61M 25/0606* (2013.01); *A61M 5/1626* (2013.01); *A61M 2005/325* (2013.01); *A61M 2005/3226* (2013.01)
(58) Field of Classification Search
 CPC ............ A61M 205/325; A61M 5/3245; A61M 25/0097
 See application file for complete search history.

(56) References Cited

U.S. PATENT DOCUMENTS

| | | | | |
|---|---|---|---|---|
| 5,599,310 | A * | 2/1997 | Bogert | A61M 25/0625 604/164.12 |
| 6,616,630 | B1 * | 9/2003 | Woehr | A61M 5/3273 604/110 |
| 8,486,024 | B2 * | 7/2013 | Steube | A61M 25/0618 604/164.08 |
| 2009/0299291 | A1 * | 12/2009 | Baid | A61M 25/0618 604/164.08 |
| 2010/0222749 | A1 * | 9/2010 | Baid | A61M 5/3273 604/263 |
| 2011/0060294 | A1 * | 3/2011 | Baid | A61M 25/0618 604/263 |
| 2012/0035552 | A1 | 2/2012 | Woehr | |
| 2013/0079720 | A1 * | 3/2013 | Finnestad | A61M 25/0618 604/164.08 |
| 2014/0180213 | A1 * | 6/2014 | Baid | A61M 5/3273 604/164.08 |
| 2015/0126931 | A1 * | 5/2015 | Holm | A61M 25/0618 604/164.08 |
| 2016/0008581 | A1 | 1/2016 | Ang et al. | |

FOREIGN PATENT DOCUMENTS

| | | |
|---|---|---|
| CN | 203090190 U | 7/2013 |
| EP | 1003588 B1 | 11/2004 |
| EP | 1920796 A1 | 5/2008 |
| EP | 2566543 A1 | 3/2013 |
| WO | WO-2010061405 A2 | 6/2010 |
| WO | WO-2013014638 A1 | 1/2013 |
| WO | WO-2013014639 A1 | 1/2013 |
| WO | WO2013/038856 * | 5/2013 |
| WO | WO2013/068856 * | 5/2013 |
| WO | WO-2013068856 A1 | 5/2013 |
| WO | 2015092041 A1 | 6/2015 |

OTHER PUBLICATIONS

International Search Report dated May 17, 2016 for PCT/SE2016/050295 in connection with related Swedish Patent Application No. 1550419-4.
International Search Report dated Mar. 10, 2005; 2015800199431.

* cited by examiner

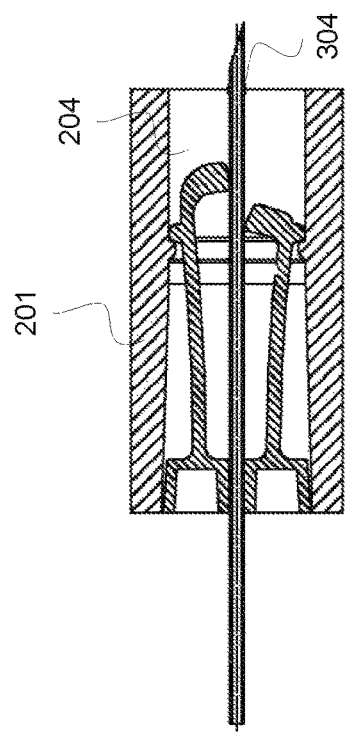
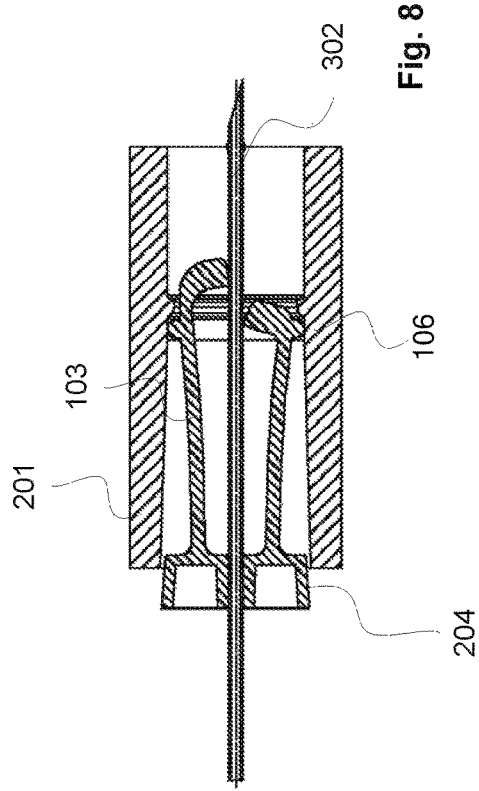
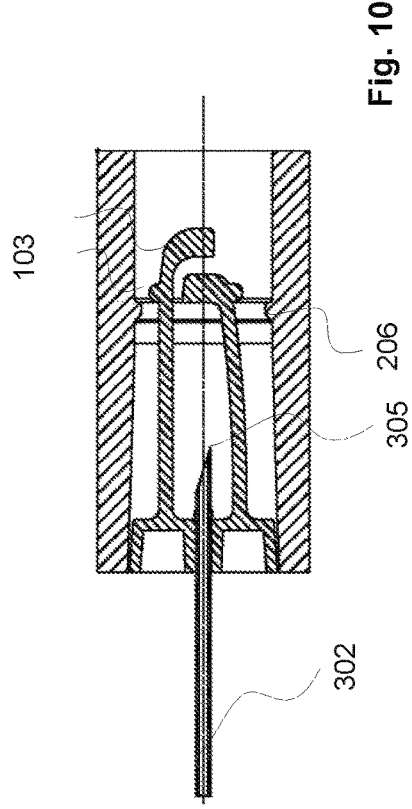

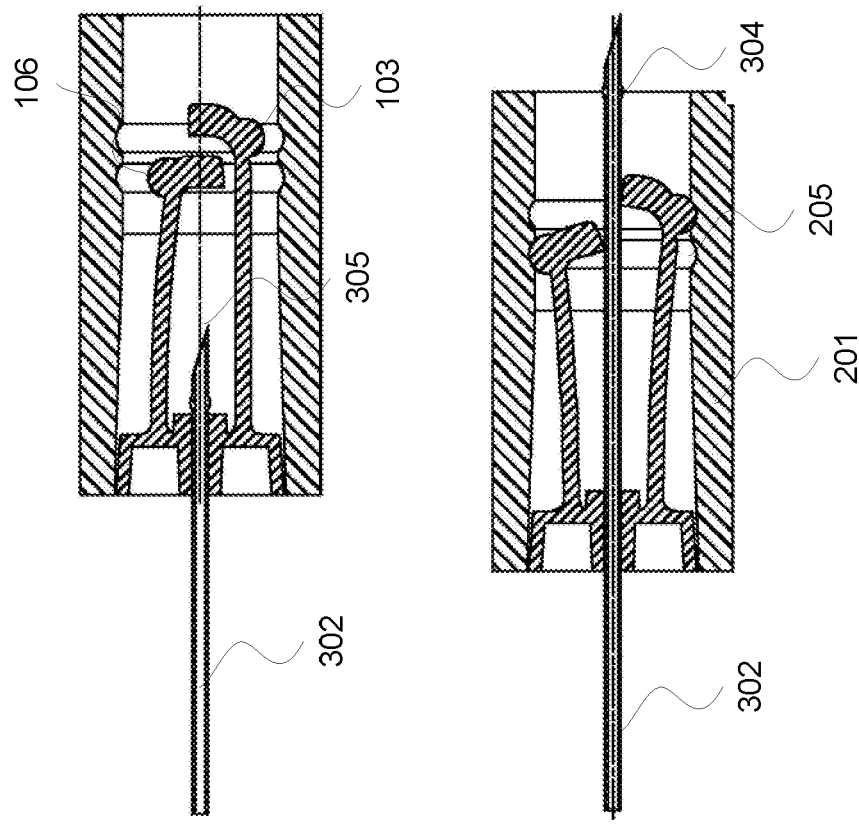
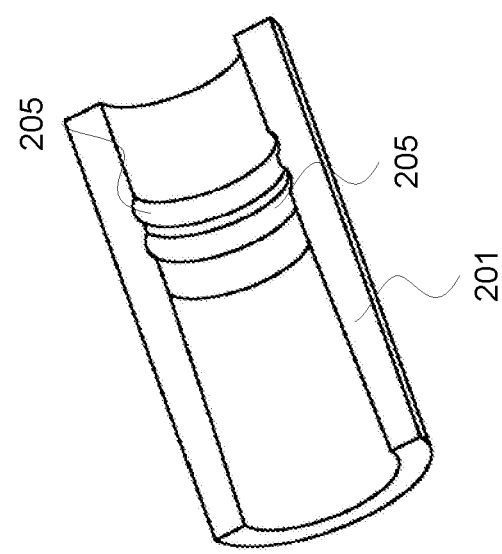

NEEDLE TIP SHIELDING DEVICE AND CATHETER HUB THEREFORE

CROSS-REFERENCE TO RELATED APPLICATIONS

This application claims priority to International Patent Application No. PCT/SE2016/050295, filed on Apr. 7, 2016, and Swedish Patent Application No. 1550419-4, filed on Apr. 9, 2015, the contents of both of which are incorporated by reference in their entireties.

TECHNICAL FIELD

The present invention relates to a needle tip shielding device for a catheter instrument comprising the needle tip shielding device, a needle hub and a catheter hub, wherein the needle tip shielding device is arranged on the needle and in the catheter hub for the automatic safety shielding of a needle after its employment for introduction of a catheter tube into the vascular system of a patient.

BACKGROUND

The clinical utilization of a pointed hollow needle mounted inside a flexible catheter tube is well known in the medical art for the introduction of a catheter. In such a medical instrument, the catheter tube is positioned tightly around the needle in such a way as to allow the needle to slide and telescope along the length of the catheter tube. Before use, the tip of the needle is protruding slightly through the opening of the catheter tube to allow facile penetration through the skin. Upon puncturing of the skin and introduction of the needle, the distal end of the catheter tube is simultaneously brought into place inside the desired target body cavity of the patient, such as the inside of a blood vessel, for example a vein. The needle has then done its duty in assisting the introduction of the catheter and is withdrawn by being pulled backwards through the catheter. Upon release of the needle, the catheter is set in its intended working mode extending over a lengthier period of time and including, for example, periodical administration or infusion of fluids or medications in liquid form, the collection of blood samples and the like.

An unprotected released needle constitutes, however, a serious health hazard due to the fact that it may be contaminated with e.g. infectious agents originating from the patient's blood or other body fluids, in combination with the needle tip's inherent ability to easily penetrate skin. Hence, the medical personnel who are handling the released needle may acquire the corresponding disease, e.g. HIV or hepatitis, if by accident contacting it with their skin. In order to circumvent or alleviate the health hazards associated with such a released needle amongst other things, there has been much effort devoted to the development of various kinds of needle tip protectors with a special focus on automatic variants of a type which may be referred to as being "foolproof".

EP 1 003 588 discloses a safety IV catheter comprising a resilient spring clip normally positioned in the catheter hub. The needle of the safety IV catheter passes through a hole in the spring clip which allows axial movement of the needle. When the needle is in the forward position, i.e. when the safety IV catheter is ready for use, the presence of the needle forces parts of the spring clip into a position where these parts locks to the inside of the catheter hub, whereby movement of the spring clip relative the catheter hub is prevented. As the needle is withdrawn to a point where the tip passes these parts, the spring clip snaps into a position in which it is blocking access to the to the tip of the needle. Simultaneously, the part of the spring clip that previously locked to the inside of the catheter hub snap out of this position, whereby movement of the spring clip relative the catheter hub may occur. As the needle is further withdrawn, means are provided, e.g. a slot or a crimp on the needle, to lock the spring clip to the needle, whereby the spring clip is ejected from the catheter hub together with, and positioned on, the needle.

For various reasons, including e.g. practical, economical and technical reasons, the above described spring clips, and similar marketed variants, are today made of metal and catheter hubs of a plastic material. Disadvantages of the combination of these materials in this application include the release of e.g. microscopic plastic chips and metallic particles by the scraping of the metal spring clip against the inside of the plastic catheter hub when the former is ejected from the latter upon withdrawal of the needle. These chips and particles may easily be flushed into the bloodstream of a patient upon normal use of the corresponding catheter, and thus represent a serious health hazard to the same. This is especially true when the spring clip needs to pass beyond a bulge or something similar within the cavity of the catheter hub, onto which the metal spring clip should be brought into retained position until being released when the needle tip passes the distal part of the metal spring clip. Another disadvantage of the spring clip of this and similar safety IV catheters is the scraping vibration generated as the needle slides through and on the spring clip as it is withdrawn. This scraping vibration, which is due to metal sliding over metal and which can be clearly heard and felt, is highly uncomfortable and worrisome to the patient, who already is in an uncomfortable and exposed situation and may be very anxious.

For these reasons attempts have been made to manufacture spring clips in materials not destroying the lumen of the catheter hub. WO2013162461 discloses a spring clip of plastic material, said spring clip interacting with the lumen of the catheter hub through a base plate thereof. However, there is a risk of the base plate interacting too much with the catheter hub lumen, since the tongues of the spring clip base plate will be in a tension state when arranged in the catheter hub.

If instead the spring clip interaction with the lumen of the catheter hub is too lax, drag from the needle shaft on the spring clip may lead to too early release of the spring clip, before the needle tip has passed the distal part of the spring clip. In effect, the spring clip would fail to protect the needle tip, constituting a serious health hazard since the practitioner might expect the needle tip to be protected.

Therefore, it would be beneficial to develop a catheter instrument with a needle protection system which ensures high product reliability while avoiding release of e.g. microscopic plastic chips.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a needle tip shielding device, comprising a base plate with a hole extending there through from the proximal side of the base plate to the distal side of the base plate, and at least one resilient arm extending at an attachment point at said base plate, wherein said at least one resilient arm has a resting state wherein a distal hook of the resilient arm will coincide with a straight imaginary line extending longitudinally through said hole in the axial direction of said base plate, said at least one resilient arm comprises a knob at its distal end, said knob extending laterally from the resilient arm; wherein said knob is shaped with an outer curvature in the transversal plane around an axis parallel to the central axis of the needle tip shielding device, and said knob is shaped with an outer curvature in the midsaggital plane around an axis perpendicular to the central axis of the needle tip shielding device.

A catheter instrument comprising such a needle tip shielding device is also provided.

Advantageous embodiments of the present invention will be apparent from the enclosed claim set.

BRIEF DESCRIPTION OF THE DRAWINGS

These and other aspects, features and advantages of which the invention is capable of will be apparent and elucidated from the following description of embodiments of the present invention, reference being made to the accompanying drawings, in which

FIG. 8 is a cross-sectional view of part of a catheter unit with a circumferential ridge and a needle with a spring clip needle tip shielding device in a unmounted, non-relaxed state;

FIG. 9 is a cross-sectional view of part of a catheter unit with a circumferential ridge and a needle with a spring clip needle tip shielding device in a mounted state;

FIG. 10 is a cross-sectional view of part of a catheter unit with a circumferential ridge and a needle with a spring clip needle tip shielding device in a relaxed state, protecting the needle tip;

FIG. 11 is a perspective view of a cross-sectional of part of a catheter unit with a two circumferential grooves;

FIG. 12 is a cross-sectional view of part of a catheter unit with two circumferential grooves and a needle with a spring clip needle tip shielding device in a relaxed state, protecting the needle tip;

FIG. 13 is a cross-sectional view of part of a catheter unit with two circumferential grooves and a needle with a spring clip needle tip shielding device in a mounted state;

DESCRIPTION OF EMBODIMENTS

Figure 2:
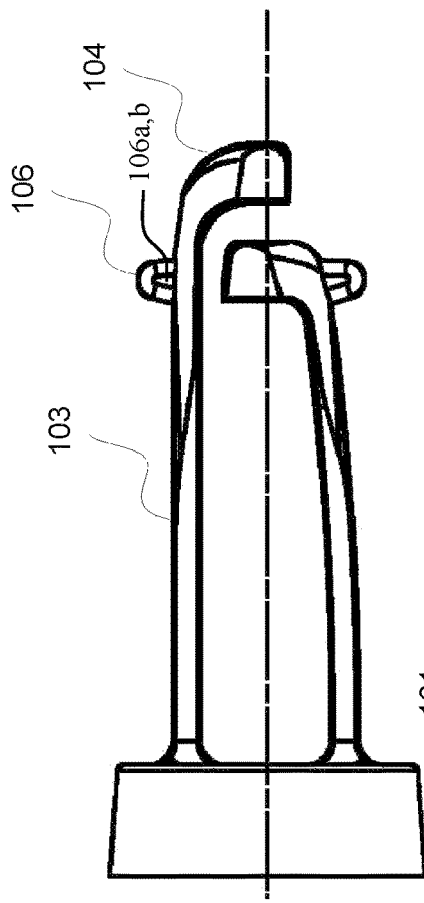
FIG. 2 is a side view of a spring clip needle tip shielding device.
Figure 4:
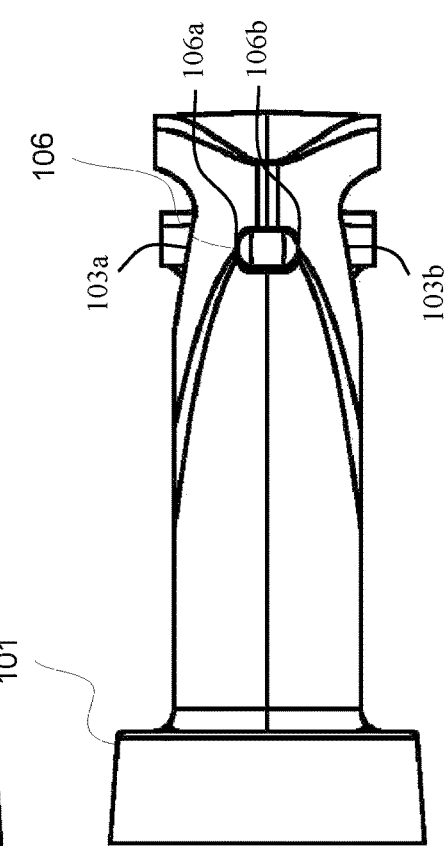
FIG. 4 is a top view of a spring clip needle tip shielding device.
Figure 1:
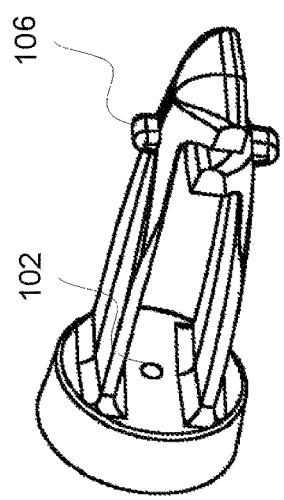
FIG. 1 is a perspective view of a spring clip needle tip shielding device.
Figure 3:
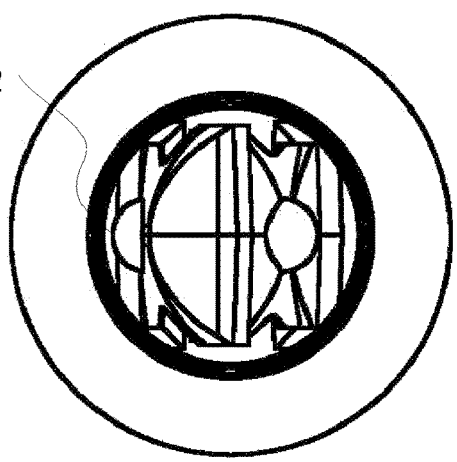
FIG. 3 is a front view of a spring clip needle tip shielding device.

Embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art.

Furthermore, the terminology used in the detailed description of the particular embodiments illustrated in the accompanying drawings is not intended to be limiting of the invention. More specifically, the term "proximal" refers to a location or direction of items or parts of items, during normal use of the IV catheter system disclosed herein, is closest to the user, i.e. the clinician, and farthest away from the patient receiving the IV catheter system. Similarly, the term "distal" refers to a location or direction of items or parts of items, during normal use of the IV catheter system disclosed herein, is closest to the patient and farthest away from the clinician. The term "laterally" refers to the direction away from the central axis of the IV catheter system, such that at least a vector component perpendicular to the central axis of the IV catheter system, wherein the needle and catheter of the assembled IV catheter system coincides with the central axis of the IV catheter system. In turn, the term "medially" refers to the direction towards the central axis of the IV catheter system, such that at least a vector component perpendicular to the central axis of the IV catheter system, wherein the needle and catheter of the assembled IV catheter system coincides with the central axis of the IV catheter system. The term "transversal plane" refers to a plane that divides the catheter system into a proximal and distal part defined by a lateral axis and an axis perpendicular to central axis of the catheter. The term "midsaggital plane" refers to a vertical plane through the midline of the catheter system, defined by the central axis of the catheter and a lateral axis.

In accordance with the present invention, FIGS. 1 to 4 show a needle tip shielding device 100, such as a spring clip needle tip shielding device 100. The spring clip needle tip shielding device 100 comprises a base plate 101. The base plate 101 is provided with a hole 102, extending there through, i.e. from the proximal side to the distal side of the base plate 101. Preferably, the hole 102 is arranged centrally on the base plate 101, such that arrangement of a needle 302 through said hole 102 is facilitated while the needle 302 is arranged in accordance with the ready position of a catheter instrument 1000.

A first resilient arm 103 is extending distally from an attachment point at said base plate 101. Preferably, due to manufacturing reasons, the attachment point is located at the periphery of the base plate 101. The at least one resilient arm 103 has a resting state, from which it may be urged into a tension state to yield free passage for the needle 302 through said hole 102 in an axial direction of said base plate 101. The resilient arm 103 is in its tension state when the catheter instrument 1000 is in its ready position. The resilient arm 103 is adapted for clamping a needle tip of a needle 302 extending through the hole 102 when the resilient arm 103 is in said resting state. For this reason, a straight imaginary line extending longitudinally through said hole 102 in the axial direction of said base plate 101 coincides with said at least one resilient arm 103 when said resilient arm 103 is in said resting state. This may be facilitated by providing the resilient arm 103 with a distal hook element 104, at the distal end of the resilient arm 103. The spring clip needle tip shielding device 100 may thus be arranged inside an interior cavity 204 of a catheter hub 201, and said needle being arranged through said hole 102 with the resilient arm 103 being urged into its tension state by said needle shaft.

The spring clip needle tip shielding device 100 is manufactured monolithically of a plastic material, with good flexibility and tension maintaining characteristics, such as polycarbonate, so as not to tear up the inner side of the catheter hub 201. The at least one resilient arm 103 is then dimensioned such that it may be flexed into its tension state when a catheter instrument 1000 is in its ready position.

The at least one resilient arm 103 is in turn provided with at least one knob 106. The knob 106 extends laterally outwards from the resilient arm 103. The knob 106 is placed at, or close to, the distal end of the at least one resilient arm 103. In this way, the knobs 106 may flex somewhat to facilitate cooperation between the resilient arm 103 and thus the spring clip shielding device 100, and the catheter hub 200, and also compensate for discrepancies in shape of the interior cavity 204 of the catheter hub 200. By placing the at least one knob 106 on the distal part of the resilient arm 103, the spring clip needle tip shielding device 100 will be reversibly locked into place in the catheter unit 200 while the at least one arm 103 is in a tension state, by interaction between the knob 106 and a groove 205 or ridge 206 in the catheter unit 200. Once the arm 103 reverts to resting state, that is once a needle tip 305 is pulled out from the catheter 202 and into the needle tip shielding device 100, the needle shield 101 will clamp itself around the needle tip 305, thus the at least one arm 103 of the needle shield 100 will revert into resting state. As this happens, the knob 106 will release contact with the groove 205 or ridge 206 in the catheter unit 200, thus unlocking from the catheter hub 201 first when the needle tip 204 is safely protected.

The at least one knob 106 has an outer curved shape, an outer curvature in the transversal plane around an axis parallel to the central axis of the spring clip needle tip shielding device 100. The outer curvature has endpoints 106a and 106b. The outer curvature in the transversal plane ensures that interaction between the knob 106 and functional elements, such a groove or ridge in the catheter hub 201, can take place without undue scratching of deformity of the knob 106, catheter hub 201 or groove 205 or ridge 206. This also ensures a smoother and more consistent function of the needle clip shielding device. If the knob 106 were to include sharp corners in the transversal plane, several shortcomings will become obvious during operation. The force during release of the needle shield from the catheter hub would be concentrated to a sharp corner on the knob 106, interacting with the catheter hub 201. With a low modulus of elasticity (polymer (PC) 2300 MPa or (LCP) 7000 MPa), the sharp corner of the knob 106 might act as a hook until it deforms or breaks (requiring more force) or flex (requiring less force). Such inconsistent behavior would thus endanger safe function.

Furthermore, the at least one knob 106 has an outer curved shape, an outer curvature, in the midsaggital plane 107 around an axis perpendicular to the central axis of the spring clip needle tip shielding device 100.

The interior of the catheter hub 201 is circular in the midsaggital plane, the corresponding curved shape in the midsagital plane 107 of the knob 106 spreads out interaction forces to a larger area. With a spring clip needle tip shielding device 100 and catheter hub 201 both made from a polymer with a modulus of elasticity (polymer (PC) 2300 MPa or (LCP) 7000 MPa), the larger area interaction results in flexing of the materials, without any persisting deformity or scraping.

This becomes extra obvious for needle guards made from a folded metal sheet, such as in EP 1 003 588, where a metal sheet is bent into a clip which inherently leads to a flat surfaces with sharp corners at the bending points. A polymer body of a catheter unit 200 has a substantially lower modulus of elasticity (polymer (PC) 2300 MPa or (LCP) 7000 MPa), compared to the modulus of elasticity of a metal clip (210 000 MPa). As such, the sharp metal corners will not deform, instead the surface of the catheter hub will be scraped by the hard metal clip during interaction.

Figure 5:
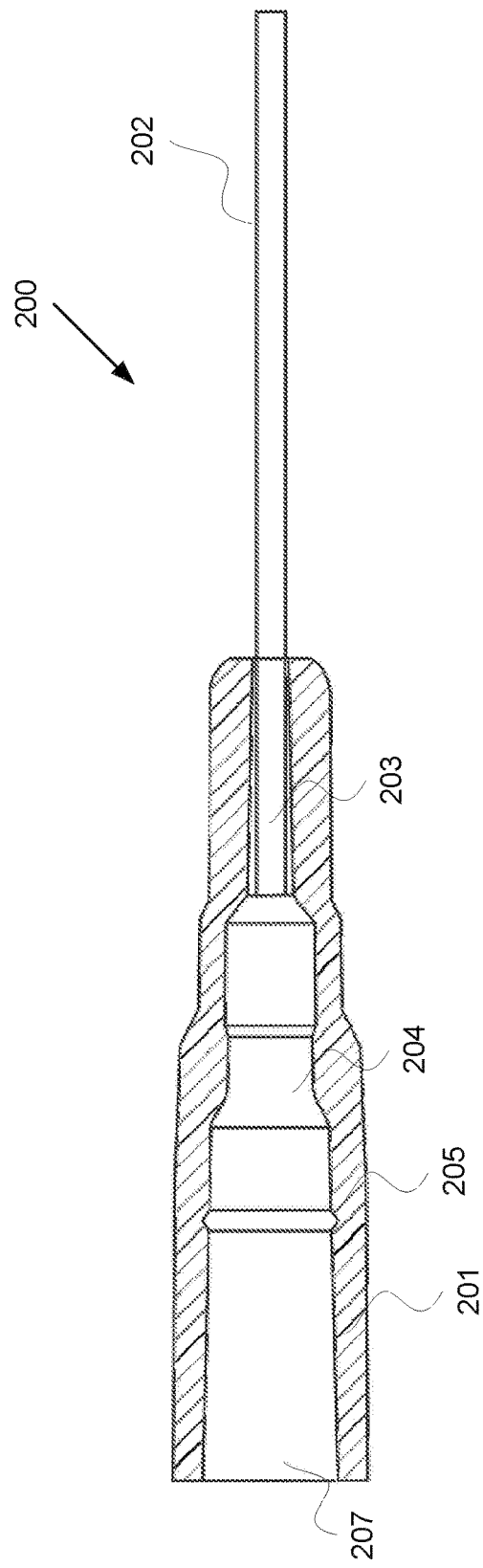
FIG. 5 is a cross-sectional view of a catheter unit.
Figure 7:
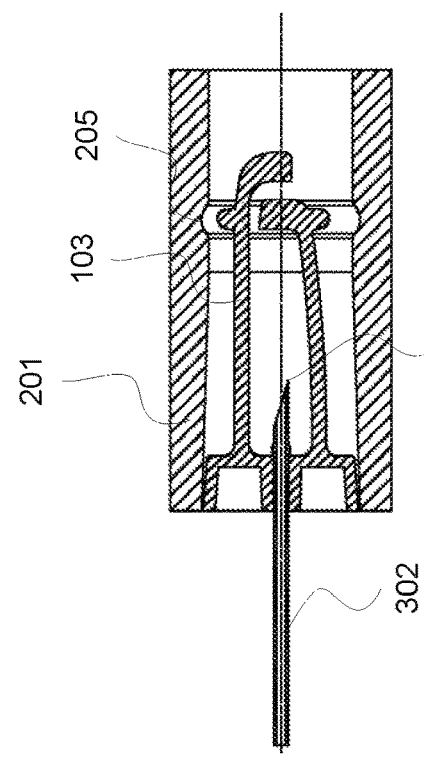
FIG. 7 is a cross-sectional view of part of a catheter unit with a circumferential groove and a needle with a spring clip needle tip shielding device in a relaxed state, protecting the needle tip.
Figure 6:
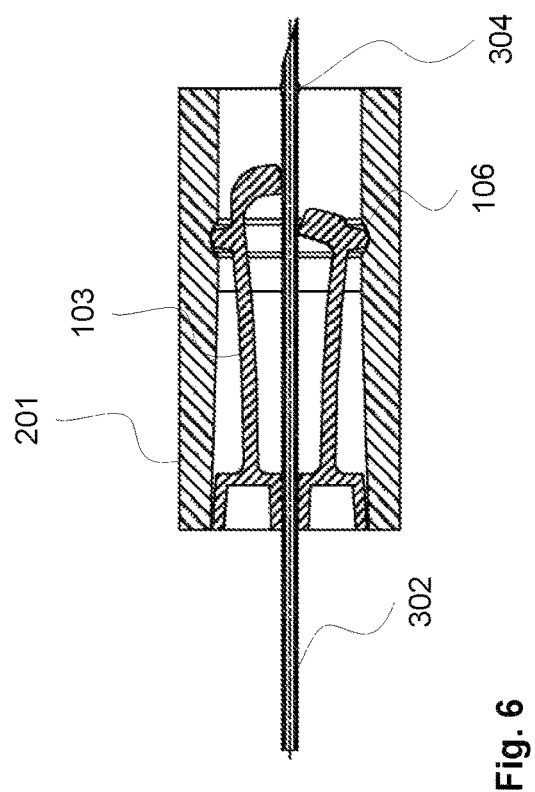
FIG. 6 is a cross-sectional view of part of a catheter unit with a circumferential groove and a needle with a spring clip needle tip shielding device in a mounted state.
Figure 14:
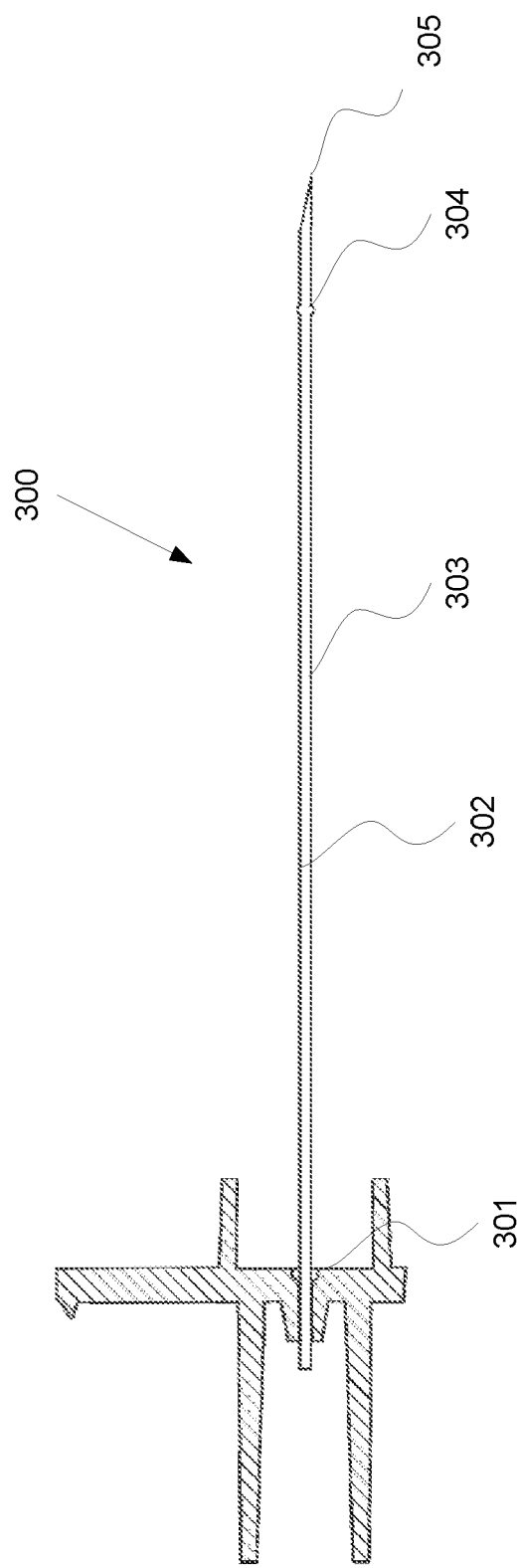
FIG. 14 is a cross-sectional view of a needle unit.
Figure 15:
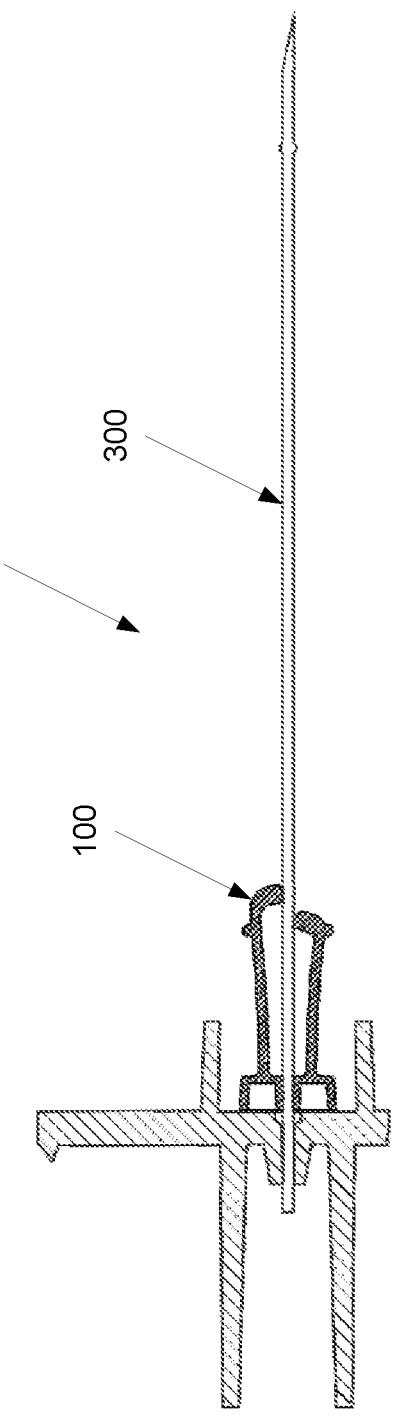
FIG. 15 is a cross-sectional view of a needle system comprising a needle unit and a spring clip needle tip shielding device.

FIGS. 5 to 7 show an example of a catheter unit 200 comprising a catheter hub 201 and a catheter 202 extending distally from the catheter hub 201. The catheter 202 is hollow and tubular, and configured to house a needle 101 stem therein. The catheter unit 200 may also be a catheter unit for an open or closed catheter system.

The catheter 202 is made of a suitable polymeric material. The catheter hub 201 is also made of a suitable polymeric material, such as polypropylene or polyethylene, which are cheap plastic materials with good injection molding properties. The hollow and tubular configuration of the catheter 202 provides a lumen 203 that is in flow communication with an interior cavity 204 of the catheter hub 201. The interior cavity 204 is positioned in the proximal end of the catheter hub 201, and the proximal opening into the interior cavity 204 may end in a luer fitting, such as a luer lock or luer slip, adapted to receive a tubing set, which in a known manner, administers intravenous fluid into the patient. The catheter unit 200 thus comprises a catheter hub 201 and a catheter 202 extending distally from the catheter hub 201, said catheter 202 having a lumen 203 being in flow communication with an interior cavity 204 of the catheter hub 201. The catheter 202 is secured within an axial passageway in the distal hub section by means of a sleeve received within passageway, which engages the proximal end of the catheter 202. This passageway communicates at its proximal end with interior cavity 204, which also acts as a flash chamber, formed in catheter hub 201. The distal end of the catheter 202 may be tapered, to facilitate introduction into the vein of the patient.

The interior cavity 204 of the catheter hub 201 may be equipped with at least one circumferential groove 205 or ridge 206 on the interior cavity 204 wall of the catheter unit 200.

As can be seen in FIGS. 6 to 7, the at least one circumferential groove 205 extends radially from the interior cavity 204 into the walls of the catheter hub 201, around the central axis of the catheter unit 200. The depth of the circumferential groove 205 is 0.05 to 0.1 mm. The groove 205 is positioned at the same distal distance from the proximal side of the catheter hub 201, as the distance from the proximal side of the base plate 101 to the knob 106 of the needle shield.

In the case of at least one circumferential ridge 206, as can be seen in FIGS. 8 to 10, the ridge 206 extends medially, around the central axis from walls of the catheter hub 201 into the interior cavity 204. The height of the circumferential ridge 206 is 0.05 to 0.1 mm The ridge 206 is positioned at a distal distance from the proximal side of the catheter huh 201, shorter than the distance from the proximal side of the base plate 101 to the knob 106 of the needle shield, such as 0.1 to 1 mm shorter.

The at least one groove 205 or ridge 206 interacts with the at least one knob 106 of the needle shield 100. The outer curvature in the transversal plane 446 of the knob 106 ensures that interaction between the knob 106 and the groove 205 or ridge 206 takes place without undue scratching of deformity of the knob 106, catheter hub 201 or groove 205 or ridge 206. This also ensures a smoother and more consistent function of the needle clip shielding device.

When receiving the spring clip shielding device 100 in the interior cavity 204 of the catheter hub 201, the spring clip shielding device 100 will be urged centrally and distally into the catheter hub 201. The spring clip shielding device 100 reaches its inserted position once the needle shield 100 base plate 102 is fully inserted. When the needle shield 100 is fully inserted, the knob 106 on the at least one arm 103 is in position to interact with the at least one circumferential groove 205, as disclosed in FIGS. 3, 4, 5 and 6. Similarly, when the interior cavity 204 of the catheter hub 201 is equipped with at least one circumferential ridge 206, the knob 106 on the at least one arm 103 is in position to interact with the catheter hub 200 when the needle shield 100 is fully inserted.

By placing the at least one knob 106 on the distal part of the resilient arm 103, the spring clip needle tip shielding device 100 will be reversibly locked into place in the catheter unit 200 while the at least one arm 103 is in a tension state, forcing the knob 106 into contact with a groove 205 or ridge 206 in the catheter unit 200. The needle shaft 303 mounted through the spring clip shielding device 100 will exert a lateral pressure on the at least on resilient arm 103, pushing it outwards towards the catheter wall, when mounted in the catheter hub 201. Thus, the knob 105 will snap into the circumferential groove 205 or in behind the ridge 206. This will. safeguard that the needle shield 100 is not unintentionally released from the catheter unit 200 until the needle tip 304 has passed into the safety of the needle shield 100. Once a needle tip 204 is pulled proximally out from the catheter 202 and into the needle tip shielding device 100, the needle shield 101 will clamp itself around the needle tip 204, thus the at least one arm 103 of the needle shield 100 will revert into resting state. As this happens, the knob 106 will release contact with the groove 205 or ridge 206 in the catheter unit 200, thus the needle shield 100 will unlock from the catheter hub 201 first when the needle tip 204 is safely protected facilitating easy release of a protected needle from the catheter hub.

FIG. 6 shows the needle shield being fully inserted into the interior cavity 204 of the catheter hub 201. Here, the knobs 105 have snapped into the corresponding grooves of the catheter hub 201. The interaction between the grooves 205 and knobs 106 safely maintains the needle shield 100 in mounted position.

FIG. 7 shows the needle shield in an inserted position, with the needle 302 retracted to a position proximal to the hooks 104 of the resilient arms 103, whereby the pressure from the needle on the resilient arms is released, enabling the resilient arms to move to a relaxed position.

A needle unit 300 comprises a needle hub 301 and a needle 302, where the needle 302 extends distally from the needle hub 301. The needle hub 301 may have an axial opening for receiving the proximal end zone of the needle 302. The needle 302 comprises a needle shaft 303 and a needle tip 305, said needle tip 305 forming the distal end point of the needle unit 300. The needle hub 301, as is conventional, may be hollow and may include a flash chamber at its proximal end. As is also conventional, the needle 302 is received within a hollow tubular catheter 202, the proximal end of which is concentrically affixed within the distal end of a catheter hub 201. At the distal end zone of the needle shaft 303, the needle 302 is provided with a bulge 304 and a needle tip 305. The needle unit 300 thus comprises a needle hub 301 and a needle 302 with a needle shaft 303, a bulge 304 and a needle tip 305 extending distally from the needle hub 301.

A needle system 400 comprises a needle hub 301, a needle 302 and a spring clip shielding device 100 according to the present invention. The spring clip shielding device 100 is mounted on the needle shaft 303 and positioned between the needle hub 301 and the needle bulge 304.

Figure 16:
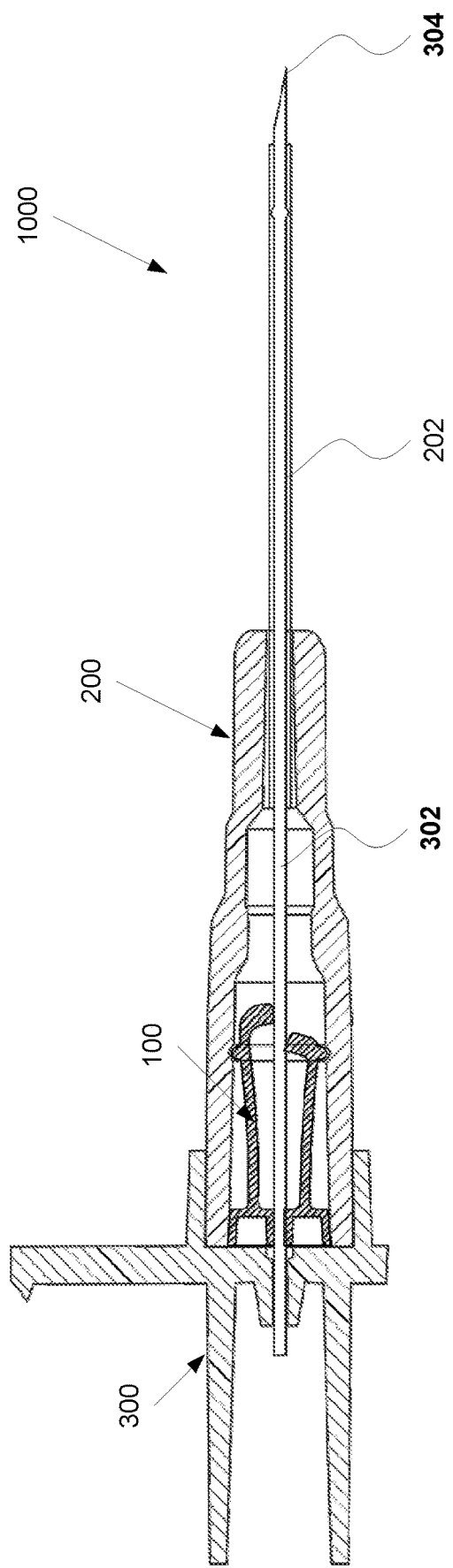
FIG. 16 is a cross-sectional view of a catheter instrument according to the present invention, comprising a spring clip needle tip shielding device, a catheter unit and a needle unit.
Figure 17:
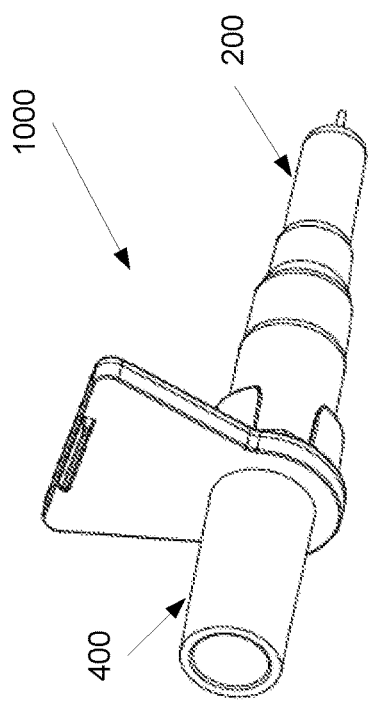
FIG. 17 is a perspective view of a catheter instrument.

FIGS. 16 and 17 shows an example safety IV catheter instrument 1000 in accordance with the present invention, comprising the spring clip needle tip shielding device 100, a catheter unit 200 and a needle unit 300, according to the present invention. The safety IV catheter instrument may also be an open or closed catheter system.

In the ready position of the catheter instrument 1000, the proximal end of the catheter hub 201 is snugly and releasably received in the distal end of the needle hub 301, such that the needle 302 extends through the cavity 204, the passageway and distally beyond the catheter hub 201 and catheter 202 so that the needle tip extends beyond a the distal end of the catheter 202. Thus, the needle hub 301 is connected to the proximal end of the catheter hub 201 and said needle shaft is arranged in the lumen 203 of the catheter 202, in a ready position of said catheter instrument 1000. The needle hub 301 may be connected to the proximal end of the catheter hub 201 and said needle shaft being arranged in the lumen 203 of the catheter 202, in a ready position of said catheter instrument 1000.

In use, the distal tip the needle 302 and the catheter 202 are inserted into a patient's vein. Thereafter, the health care practitioner manually places the catheter 202 further into the vein and then withdraws the needle by grasping and moving by hand the proximal end of the needle unit 300. In the example safety IV catheter instrument 1000, the luer of the catheter hub 200, in the proximal end of the cavity 204, is then fitted with a source of the fluid that is to be administered into the patient's vein.

After the distal tip of the needle 302 and the catheter 202 have been inserted into a patient's vein, the needle unit 300 is displaced proximally in relation to the catheter unit 200 and the spring clip needle tip shielding device 100. The spring clip needle tip shielding device 100 is retained in the catheter hub 201 of the catheter unit 200 through interaction between the base plate 102, in accordance with above. When the needle unit 300 is displaced proximally in relation to the catheter unit 200 and the spring clip needle tip shielding device 100, also the needle 302 is displaced proximally in relation to these two. Once the needle tip passes proximally beyond the distal end of the resilient arm 103, such as the hook element 104, the distal end of the resilient arm 103 snaps in front of the needle tip. The bulge on the needle shaft then hits the base plate 102, since the bulge has been dimensioned with a somewhat larger diameter than the through hole of the base plate 102. Also, the bulge has been positioned on the needle shaft at a distance from the needle tip largely corresponding to the distance between the base plate 102 and the distal end of the resilient arm 103, such that the spring clip needle tip shielding device 100 may be secured at the distal end of the needle 302 once the needle tip has been displaced proximally beyond the distal end, such as the hook element 104, of the spring clip needle tip shielding device 100. In this position, the spring clip needle tip shielding device 100 is released from the catheter unit 200 through overcoming the frictional force between the base plate 102 and the interior wall of the catheter hub 201, in accordance with above. The interaction reversible interlocking between the knob 105 and the groove 205 or ridge 206 in the catheter unit 200 will ensure that the needle shield is not released until the needle shield 300 is securely arranged on the tip of the needle 304 to prohibit and prevent accidental needle stick, as can be seen in FIGS. 7,10, and 12.

FIGS. 11 to 13 shows a configuration in which the needle shield 100 is mounted on the needle, the needle shaft 206 extending through the hole of the needle shield base plate, the base plate being at the proximal end and two resilient arms 103 at the distal end. As can be seen in FIGS. 12 and 13, each resilient arm 105 of the needle shield 100 has a knob 105 at the distal side of the resilient arm 103, extending laterally. Two corresponding grooves 205 run along the inner radius of the needle hub 201 interior cavity 204, laterally to the extension of the needle 302. The knobs 105 are at different distances from the proximal end of the needle shield 100, and the distances correspond to the distances between the two grooves 205 and the proximal end of the catheter hub 200, respectively.

FIG. 12 shows the shield in an inserted position, with the needle retracted to a position proximal to the hooks 104 of the two resilient arms 103, whereby the pressure from the needle 302 on the resilient arms 102 has been released, enabling the resilient arms 103 to be in a relaxed position.

FIG. 13 shows the needle shield being fully inserted into the interior cavity 204 of the catheter hub 201. Here, the knobs have snapped into the corresponding grooves of the catheter hub 201. The interaction between the grooves 108 and knobs 105 safely maintains the needle shield 100 in inserted position.

According to one embodiment, the needle shield 100 may be made of a plastic material. Preferably, the plastic material has a suitable combination, for its intended purpose, of tenacity, rigidity, fatigue resistance, elasticity, and creep deformation resistance. A suitable plastic material has a high creep deformation resistance, i.e. it has a low tendency to slowly move or deform permanently under the influence of an applied external pressure. Hence, a catheter system 1000 of the present invention, comprising needle shield 100, may be stored in the assembled ready mode for a prolonged time without extensive creep deformation of the arms 103 or the knobs 105. Advantages of a plastic needle shield 100 include the highly reduced tendency, in comparison to metal, of release of e.g. microscopic plastic chips by the scraping of the plastic catheter hub 200, when the needle shield 100, is ejected from the former upon withdrawal of the needle 302. Accordingly, the tendency for formation of scrape marks, which may result in leakage through the affected connector, is greatly reduced. In addition, a plastic needle tip shielding device 100 may be easily color coded or transparent, depending on its particular application.

The needle shield 100 is a monolithic or homogenous injection molded needle shielding 100, made of a molded plastic material. Due to the specific configuration of the different parts of the needle shield 100 according to the embodiments of the present invention, the needle shield 100 may be molded, such as injection molded, into one homogenous, i.e. monolithic, piece and/or one integral unit, without interfaces in between the different parts thereof. Advantages of a monolithic needle shield 100 include a lower production cost in comparison to other devices made of more than one part that has to be assembled. The needle shield 100 may in this respect be made of a thermoplastic polymer. The thermoplastic polymer could be crystalline, amorphous, or comprising crystalline and amorphous alternating regions. A creep resistance of the thermoplastic polymer of choice may preferably be at least 1200 MPa (ISO 527, ASTM D638). Suitable plastics for the needle shield 100 may be selected from the group comprising of polyoxymethylene (POM), polybutylen terephthalate (PBTP), polymethyl methacrylate (PMMA), acrylonitrile butadiene styrene (ABS), styrene acrylonitrile (SAN), acrylonitrile styrene acrylate (ASA), polystyrene (PS), styrene butadiene (SB), liquid crystal polymer (LCP), polyimide (PA), polysulfone (PSU), polyetherimide (PEI), polycarbonate (PC), polyphenylene oxide (PPO), and/or PPO/SB, and co- and terpolymers thereof. These polymers have specifically the advantages of providing enhanced storing capacity, even in strained state, and excellent cooperation abilities with regard to the catheter hub, due to the excellent structure memory of these polymers.

Contacting smooth shapes of two bodies, such as a needle shield 100 mounted in a catheter hub 200, may result in a significant attraction between these bodies, especially if the contact area is large and they are pressed together. The underlying basis for this type of attraction include intermolecular attraction between the molecules of the two bodies, in which molecular van der Waals interactions and surface tension of the two bodies are important factors. Covalent bond formation between closely interacting surfaces may also contribute to the attraction. Such covalent bond formation, and other types of attraction between two surfaces, may also result upon radiation treatment, such as radiation treatment of e.g. catheter instrument to sterilize these. This type of attraction may become noticeable when the needle shield 100 is about to be released from the catheter hub 200. The force needed to release the needle shield 300 from the catheter hub 100 then becomes significantly higher than expected. This effect, which may be referred to as "the attraction effect", may even adventure the intended function of the needle tip shielding device 100 if relying on e.g. an automatic release of a part of the device, such as a spring biased arm or the like, from a part of the catheter hub. The needle shield 100 is kept in contact with the catheter hub 200 in the assembled state via at least one interface surface between the needle shield 100 and the catheter hub 200. Thus, in one embodiment the surface of the needle shield 100 being in contact with the inner lumen of the catheter hub is of a different polymeric material than the polymeric material of the catheter hub.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A needle tip shielding device, comprising:
   a base plate with a hole extending therethrough from a proximal side of the base plate to a distal side of the base plate, the base plate having a first wall, a second wall parallel to the first wall, and a sloped wall intersecting the first and second walls, the sloped wall is operable to engage a bore of a catheter hub, the base plate further having an outer diameter that is configured to be received within the bore of the catheter hub; and
   at least one resilient arm extending at an attachment point at said base plate, the at least one resilient arm is offset inward from the outer diameter of the base plate,
   wherein said at least one resilient arm has a resting state wherein a distal hook of the at least one resilient arm will coincide with a straight imaginary line extending longitudinally through said hole in an axial direction of said base plate,
   wherein said at least one resilient arm comprises an outer surface and a knob extending laterally from a distal end of the at least one resilient arm, and
   wherein said knob includes an outer curvature and lateral end surfaces.

2. The needle tip shielding device according to claim 1, wherein the outer curvature of said knob is configured to be received by a groove located in the catheter hub.

3. The needle tip shielding device according to claim 1, wherein a radius of the outer curvature in a transversal plane is a medial distance from the outer curvature in the transversal plane to the straight imaginary line extending longitudinally through said hole in the axial direction of said base plate, or smaller.

4. The needle tip shielding device according to claim 1, wherein a medial radius of the outer curvature in a transversal plane is 2 to 0.1 mm.

5. The needle tip shielding device according to claim 1, wherein a radius of an outer curvature in a midsagital plane is a medial distance from the outer curvature in the midsagital plane to an intersecting axis perpendicular to the straight imaginary line extending longitudinally through said hole in the axial direction of said base plate, or smaller.

6. The needle tip shielding device according to claim 1, wherein the knob is of a shape without sharp protruding edges including a half sphere or a wedge, cuboid or polyhedron with rounder corners.

7. The needle tip shielding device according to claim 1, wherein the needle tip shielding device has a first outer diameter that is larger, in a transversal plane intersecting the knob, than a second outer diameter of the base plate in a transversal plane intersecting the base plate, when the at least one resilient arm is in the resting state.

8. The needle tip shielding device according to claim 1, wherein the at least one resilient arm includes at least two resilient arms having respective first and second knobs with the same proximal distance to the base plate.

9. The needle tip shielding device according to claim 1, wherein the at least one resilient arm includes at least two resilient arms having respective first and second knobs at different proximal distances from the base plate.

10. The needle tip shielding device according to claim 1, wherein the needle tip shielding device is manufactured in polycarbonate or a copolymer of polycarbonate and polyester.

11. The needle tip shielding device according to claim 1, wherein the needle tip shielding device is injection molded.

12. A needle tip shielding device, comprising:
    a base plate with a hole extending therethrough from a proximal side of the base plate to a distal side of the base plate; and
    a first and second resilient arm extending from said base plate, the first resilient arm is longer than the second resilient arm, the first resilient arm has a distal hook extending inwardly, the second resilient arm has a distal hook extending inwardly, both arms having a resting state wherein, in the resting state of the first resilient arm, the distal hook of the first resilient arm coincides with a straight imaginary line extending longitudinally through said hole extending in an axial direction of said base plate,
    wherein the first resilient arms has a knob, said knob extending laterally from a distal end of the first resilient arm, and said knob having an outer curvature and lateral end surfaces, the outer curvature being in a transversal plane around an axis parallel to a central axis of the needle tip shielding device.

13. The needle tip shielding device according to claim 12, wherein said knob is shaped with the outer curvature in a midsagital plane around an axis perpendicular to the central axis.

14. The needle tip shielding device according to claim 12, wherein the second resilient arm includes a knob, the knob is configured to be received within a groove that is located within an interior cavity of a hub.

15. The needle tip shielding device according to claim 12, further comprising a hub with an internal groove, the knob is operable to flex and move in and out of the groove.

16. A needle tip shielding device, comprising:
    a base plate having a central axis and a hole extending from a proximal side of the base plate to a distal side of the base plate;
    a first resilient arm extending from said base plate;
    a second resilient arm extending from said base plate; and
    a hub operable to receive said first and second resilient arms, said hub having an interior cavity with a first groove and a second groove that is spaced apart axially from said first groove;
    wherein each resilient arm includes a distal hook and a knob, the knob of the first resilient arm is operable to be received within the first groove, the knob of the second resilient arm is operable to be received within the second groove, and
    wherein each knob includes an outer curvature and lateral end surfaces.

17. The needle tip shielding device according to claim 16, wherein each knob is shaped with the outer curvature in a midsagital plane around an axis perpendicular to the central axis.

18. The needle tip shielding device according to claim 16, wherein the knobs have different proximal distances to the base plate.

19. The needle tip shielding device according to claim 16, wherein the first resilient arm is longer than the second resilient arm.

* * * * *